United States Patent [19]

Popovich et al.

[11] Patent Number: 4,620,845

[45] Date of Patent: Nov. 4, 1986

[54] METHOD OF PERITONEAL DIALYSIS INVOLVING ULTRAVIOLET RADIATION OF DIALYSIS APPARATUS

[76] Inventors: Robert P. Popovich, 2928 Kassarine Pass, Austin, Tex. 78704; Jack W. Moncrief, 3633 West Lake, Austin, Tex. 78746

[21] Appl. No.: 625,801

[22] Filed: Jun. 28, 1984

Related U.S. Application Data

[62] Division of Ser. No. 270,800, Jun. 5, 1981, Pat. No. 4,475,900.

[51] Int. Cl.⁴ .............................................. A61M 3/00
[52] U.S. Cl. ....................................... 604/28; 604/905
[58] Field of Search ................. 604/28, 29, 283, 905, 604/20; 422/24

[56] References Cited

U.S. PATENT DOCUMENTS

| | | | |
|---|---|---|---|
| 4,209,013 | 6/1980 | Alexander et al. | 604/28 X |
| 4,306,976 | 12/1981 | Bazzato | 604/28 X |
| 4,412,834 | 11/1983 | Kulin et al. | 604/29 |

OTHER PUBLICATIONS

S. J. Joshi et al, "In Vitro Studies on Surface Sterilization of Continuous Ambulatory Peritoneal Dialysis Tubing Using Ultraviolet Light" Kidney International Official Journal of the International Society of Nephology, vol. 1, Jan. 1981, p. 150.

A. J. Bisinger, "A Simple Method of Lessening the Incidence of Peritonitis in Peritoneal Dialysis using a Photochemical Reactor", Clinical Nephology, vol. 14, No. 1-1980 (pp. 42-44).

*Primary Examiner*—Stephen C. Pellegrino
*Attorney, Agent, or Firm*—Arnold, White & Durkee

[57] ABSTRACT

The incidence of peritonitis is reduced in continuous ambulatory peritoneal dialysis by irradiating the peritoneum access tube connection with ultraviolet (UV) radiation so as to have an antimicrobial effect on the fluid flow path defined thereby prior to draining and infusion of dialysis fluid therethrough. The apparatus for effecting UV irradiation of the dialysis fluid flow path includes a housing for enclosing the tube connection. Contained inside the housing is a source of UV radiation for irradiating the tube connection. A UV radiation source control circuit establishes the irradiation cycle based on time of exposure. A UV radiation intensity measuring cirucit may also be used to maintain UV source output until a predetermined cumulative UV exposure has been attained.

7 Claims, 18 Drawing Figures

METHOD OF PERITONEAL DIALYSIS INVOLVING ULTRAVIOLET RADIATION OF DIALYSIS APPARATUS

This is a divisional of application Ser. No. 270,800, filed June 5, 1981, now U.S. Pat. No. 4,475,900.

BACKGROUND OF THE INVENTION

The present invention relates generally to fluid infusion methods for performing peritoneal dialysis on a patient, especially continuous ambulatory peritoneal dialysis (CAPD). The present invention further relates to methods and apparatus for preventing peritonitis in a patient undergoing peritoneal dialysis treatment.

In the treatment of patients suffering acute or a chronic renal insufficiency due to loss of normal kidney function, dialysis therapy is employed. The two general categories of dialysis therapy are hemodialysis and peritoneal dialysis. In hemodialysis, a patient's blood is cleansed by passage through an artificial kidney. In peritoneal dialysis, dialysis fluid is infused into the patient's peritoneal cavity, which is lined by the peritoneal membrane, and metabolites are removed from the patient's blood by diffusion across the peritoneal membrane; water is also removed because of the osmotic effect of the dialysis fluid.

Within the general category of peritoneal dialysis, modern application has resulted in several peritoneal dialysis techniques. Foremost among the peritoneal dialysis techniques are standard intermittent peritoneal dialysis (IPD) and continuous ambulatory peritoneal dialysis (CAPD).

The usual clinical procedure for a patient beginning peritoneal dialysis, after the surgical implantation of a catheter into the peritoneal cavity, involves infusion of dialysis fluid into the peritoneal cavity of a patient, where it is allowed to equilibrate for a period of time and then drain from the peritoneal cavity.

IPD is performed intermittently, with intensive treatments being conducted two to four times per week. In each treatment, dialysis fluid is rapidly infused and allowed to equilibrate for up to 90 minutes, after which it is removed.

IPD is performed using clamps, connection tubing, and exchange containers, the manipulation of which entails careful and time-consuming attention by a competent nursing staff. The frequent handling of fresh and waste dialysis fluid bottles and the connection apparatus presents a substantial risk of infection to the peritoneum. Because of the high risk of infection, and because trained personnel need to be available to perform IPD, IPD has not gained widespread usage. In an attempt to reduce the risk of infection and minimize nursing time, automatic dialysis fluid cycling equipment for automating the dialysis procedure has been adopted in many instances.

Continuous ambulatory peritoneal dialysis (CAPD), which is a recent medical discovery, differs from IPD. In CAPD, multiple dialysis fluid exchanges are performed daily with a significantly longer interval between exchanges being employed when compared with IPD, such that a substantially constant presence of dialysis fluid is maintained within a patient at all times. A description of the continuous ambulatory peritoneal dialysis technique may be found in Popovich, et al. U.S. Pat. No. 4,239,041, issued Dec. 16, 1980 and entitled "METHOD FOR CONTINUOUS AMBULATORY PERITONEAL DIALYSIS."

To perform CAPD, an in-dwelling catheter capable of having a peritoneum access tube connected thereto is implanted in the peritoneal cavity. A dialysis solution bag containing about two liters of dialysis solution is attached to the free end of the tube, and the fluid is infused into the peritoneal cavity. The dialysis solution bag is preferably plastic and flexible. Dianeal ® dialysis solution in plastic, flexible bags is manufactured and sold by Travenol Laboratories, Inc., Deerfield, Ill. and may be used in practicing CAPD.

After infusion, the access tube is clamped off and the patient folds up the empty bag, which is then carried by the patient while dialysis takes place. Alternatively, the empty bag can be disconnected from the access tube and a cap placed on the external coupling connector at the end of the access tube; when the patient thus "caps off", the patient may use glass or plastic bottles of dialysis solution as an alternative to the preferred plastic bags since a primary benefit of the plastic bags is that they can be rolled for carrying by the patient while dialysis takes place.

After the period of dialysis fluid residence (dwell), the patient, if wearing the bag, unwraps the empty plastic bag, lowers it to the floor, releases the clamp and lets the waste-laden dialysis fluid drain out of the peritoneal cavity. Next a new bag of fluid is attached, and fresh fluid is infused into the peritoneal cavity. If the patient is not wearing the empty bag during dwell, the cap on the end of the supply tube is removed and a drainage bag or other suitable container is attached thereto. After draining of fluid from the peritoneal cavity, a new bag of fresh fluid is attached and the fresh fluid is infused.

Continuous ambulatory peritoneal dialysis permits a patient to carry out his normal daily activities while dialysis is taking place. Also, because CAPD is much simpler than IPD, a patient can readily administer the treatment himself at home.

For many years, peritonitis has been a complication of long-term peritoneal dialysis for end-stage kidney disease. With CAPD, the risk of peritonitis is reduced, but improved infusion methods and apparatus are needed to permit CAPD to reach its full potential. The present invention seeks to reduce the incidence of infection in peritoneal dialysis procedures in general and in continuous ambulatory peritoneal dialysis in particular.

SUMMARY OF THE INVENTION

In accordance with the present invention, the risk of infection to a patient undergoing peritoneal dialysis treatment is substantially reduced by irradiating with UV radiation potentially contaminable portions of the dialysis fluid exchange apparatus to thereby have an antimicrobial effect on the same.

The present invention is particularly advantageous for continuous ambulatory peritoneal dialysis (CAPD), since a patient undergoing CAPD typically administers the treatment to himself at home. However, the present invention is also effective to reduce like infection hazards associated with conventional intermittent peritoneal dialysis, whether carried out using a gravity flow set or an automatic dialysis fluid cycling machine.

A method of peritoneal dialysis therapy for a patient in accordance with the present invention involves the patient connecting a source of dialysis fluid to the peritoneum access tube and irradiating the connection between the access tube and fluid source with ultraviolet radiation prior to infusing dialysis fluid into the peritoneal cavity. The method of the present invention may be utilized when the source of dialysis fluid is a container having an outlet tube for connection to the peritoneum access tube; in this situation, the potential contamination zone adjacent the connection of the access tube and container outlet tube is irradiated with ultraviolet radiation. Dialysis fluid is then infused into the patient through the access tube.

If desired, irradiation may continue during infusion of fresh dialysis fluid.

Typically, in CAPD, the container is a plastic bag which remains attached to the access tube after infusion of fresh dialysis fluid, and is rolled-up and carried by the patient while the fluid is in the peritoneal cavity for a residence time period (dwell). After the residence period, the fluid is drained into the empty bag, and the bag is then disconnected. The aforementioned steps of connecting a new bag, irradiating the connection, and infusing fresh fluid are then repeated.

Sometimes, however, it might be desired to disconnect the container from the access tube after infusion. In that case, prior to draining the spent fluid, an empty container is connected to the access tube, and to avoid possible infection, preferably the connection between the empty container and the access tube is irradiated with ultraviolet radiation. Then, spent dialysis fluid may be drained through the connection into the empty bag.

BRIEF DESCRIPTION OF THE DRAWINGS

A written description setting forth the best mode presently known for carrying out the present invention, and of the manner of implementing and using it, is provided by the following detailed description of illustrative embodiments, which refers to the accompanying drawings wherein.

DETAILED DESCRIPTION OF ILLUSTRATIVE EMBODIMENTS

Figure 1:
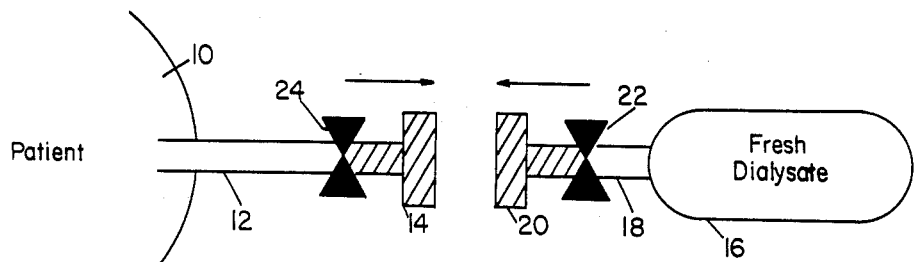
FIG. 1 is a schematic diagram of a patient having a peritoneum access tube to which a bag of fresh dialysis fluid is being connected.

Referring to the drawings, a patient 10 undergoing continuous ambulatory peritoneal dialysis (CAPD) has a fluid flow path established to his peritoneal cavity. Suitably, the fluid flow path is established by a catheter system comprising a surgically-implanted indwelling catheter 11 having mated to it a connecting tube 12 which terminates at a mating connector 14. The peritoneal catheter 11 may be, for example, a Tenckhoff catheter. Tube 12 is connected to catheter 11 by means of connector 15 integral with catheter 11 mating with connector 17 which is integral with one end of tube 12. Since the connection formed by connector 15 mating with connector 17 does not relate specifically to applicants' invention, for purposes of clarity it is not shown in FIGS. 2-9; the presence of the connection and catheter 11 in FIGS. 2-9 should, however, be inferred. Additionally, for simplicity in referencing the fluid flow path establishing means comprising the catheter 11, tube 12 and connectors 14, 15 and 17, the terminology "peritoneum access tube" will occasionally be used in the description which follows.

As indicated by FIG. 1, a method of peritoneal dialysis therapy in accordance with the present invention proceeds with a source of fresh dialysis fluid being connected to the peritoneum access tube. As shown in FIG. 1, the source of fresh dialysis fluid may suitably be a bag 16 having an outlet tube 18 which terminates at a connector 20. Connector 20 is adapted for mating connection with connector 14 of the peritoneum access tube. Connectors 14 and 20 are suitably a Luer-lock type connector. Bag 16 suitably has a volume capacity of about 2 liters for adults. Alternatively, the source of fresh dialysis fluid may be another form of container, such as a glass bottle. Also, the source of fresh dialysis fluid could be a fluid dispensing or cycling machine.

As shown in FIG. 1, outlet tube 18 and tube 12 are both closed by pinch-type clamps. Specifically, clamp 22 provides a means of opening and closing outlet tube 18, and clamp 24 provides a means of opening and closing tube 12 to fluid flow. With clamps 22 and 24 closing their respective tube, the connectors 14 and 20 at the end of their respective tube and that portion of the tube between the connectors and the clamps is susceptible to bacterial contamination; this portion will be referred to as a "potential contamination zone", and is indicated in FIG. 1 by the crosshatching.

Figure 2:
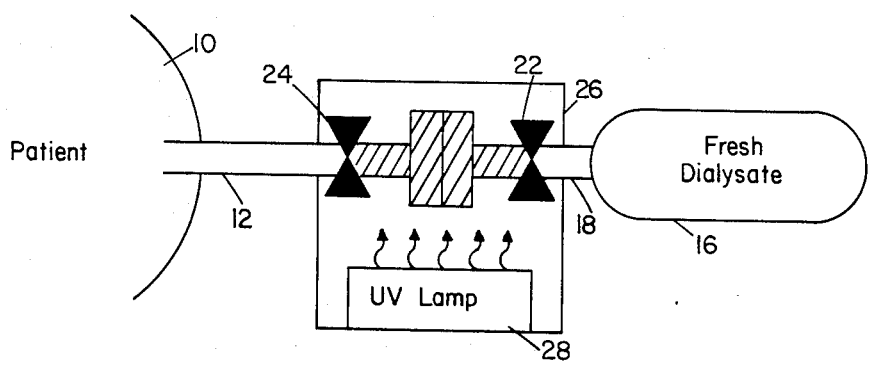
FIG. 2 illustrates irradiation with ultraviolet light of the connection of the bag and tube to have an antimicrobial effect on the same.

Referring next to FIG. 2, after connecting bag 16 to the peritoneum access tube, by engaging connector 14 with connector 20, at least the potential contamination zone is exposed to ultraviolet radiation to have an antimicrobial effect on the zone. Suitably, the potential contamination zone is exposed to ultraviolet radiation by irradiation with ultraviolet light in the wavelength range of 2400-2800 Angstroms, which is a known antimicrobial wavelength range of UV. The light should be of sufficient intensity to penetrate the connectors and tubing segments, so as to reach all internal surfaces which may come into contact with dialysis fluid being infused into the patient.

The required total antimicrobial ultraviolet radiation exposure is, of course, dependent upon the type and number of microorganisms to be killed. As an example, consider *Asporgillus niger* in a concentration of $3.6 \times 10^5$ spores/ml. To achieve a 99% kill, a total UV radiation exposure dosage of up to 527,540 $\mu$Ws/cm$^2$ would be required.

The total UV radiation exposure dosage is a product of the intensity of the radiation and the time of exposure. Accordingly, by dividing the dosage by exposure time, the required UV intensity can be calculated. Because incident radiation intensity is affected by the focussing geometry between the UV source and the potential contamination zone, and by the UV transmittance of the materials used for the tubes and connectors, the transmittance impedances of these items must be taken into consideration in determining the required lamp output intensity. It is reasonable to expect that a 50% loss in lamp output intensity will result in most cases.

Finally, UV intensity is a function of total output power from the UV source and the surface area being irradiated. Thus, to determine lamp output power, the surface area to be irradiated must be calculated.

Assuming a length of tubing 11.5 inches long and $\frac{1}{4}$ inch in diameter to be irradiated, the surface area is 58.27 cm$^2$. To produce a dosage of 527,540 $\mu$Ws/cm$^2$ with a 60 seconds exposure time, the intensity required would be 8,792 $\mu$W/cm$^2$. If there is a 50% power loss, the required lamp output intensity would be 17,584 $\mu$W/cm$^2$. Thus, the lamp output power would have to be about 1 watt.

Irradiation of the potential contamination zone may be accomplished by placing the portion of tubes 12 and 18 between clamps 22, 24, as well as clamps 22 and 24 themselves, in a UV light box 26 having a UV lamp 28. Suitably, lamp 28 may be a mercury vapor lamp.

Connectors 14 and 20, tubes 12 and 18 and clamps 22, 24 must be made of a material which is transmissive to ultraviolet radiation in the 2400-2800 Angstroms wavelength range. Suitable materials include polycarbonate, polyvinylidene fluoride, FEP-Teflon ®, and polyvinylchloride.

Figure 3:
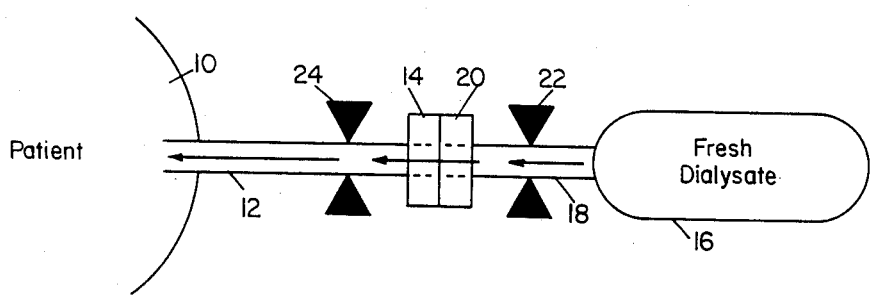
FIG. 3 illustrates the infusion of fresh dialysis fluid from the bag into the patient.

As indicated in FIG. 3, after irradiation of the potential contamination zone, clamps 22 and 24 are released so that dialysis fluid may be infused from bag 16 through the peritoneum access tube into the patient's peritoneal cavity.

It will, of course, be understood that although FIG. 3 indicates that infusion takes place after removal of the connection and tubing from light box 26, ultraviolet irradiation may continue during dialysis fluid infusion if so desired.

Figure 5:
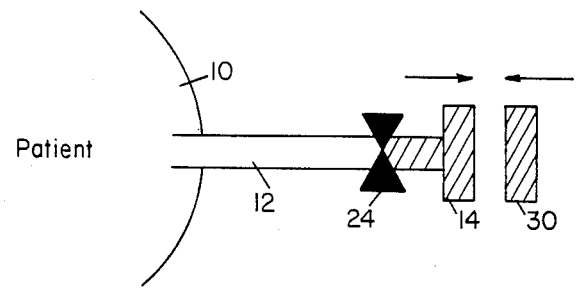
FIG. 5 illustrates the capping of the access tube after disconnection of the empty bag.
Figure 4:
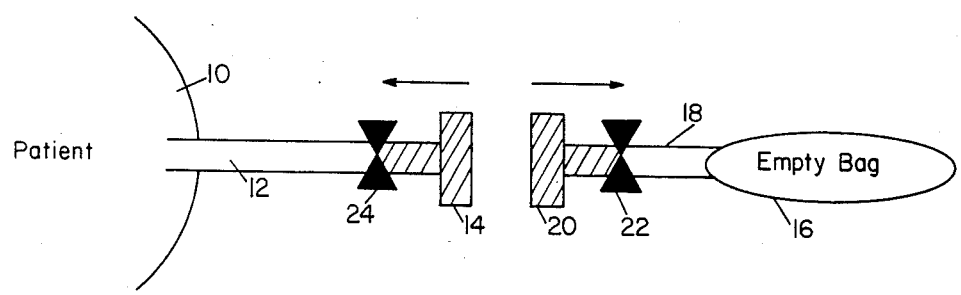
FIG. 4 illustrates the disconnecting of the empty bag after infusion.

After infusion of fresh dialysis fluid, tube 12 is clamped off at clamp 24. Bag 16 and the interconnected tubes 12 and 18 may be rolled-up and carried by the patient under his clothes. Alternatively, as indicated in FIG. 4, the empty bag 16 may be disconnected from the peritoneum access tube by disconnecting connector 20 from connector 14. If such a disconnection is made, then preferrably, as indicated in FIG. 5, a cap 30 is placed on connector 14.

After the desired period of residency within the peritoneal cavity, the dialysis fluid must be drained. If the bag which carried fresh dialysis fluid has been rolled-up and carried by the patient, then drain of dialysis fluid is readily accomplished by unrolling the bag and unclamping the peritoneum access tube and bag outlet tube at clamps 24 and 22, respectively. Then, after draining the fluid, tube 12 is again clamped at clamp 24, and the bag is disconnected from the peritoneum access tube. The steps shown in FIGS. 1-3 are then repeated to refill the peritoneal cavity with fresh dialysis fluid.

Figure 7:
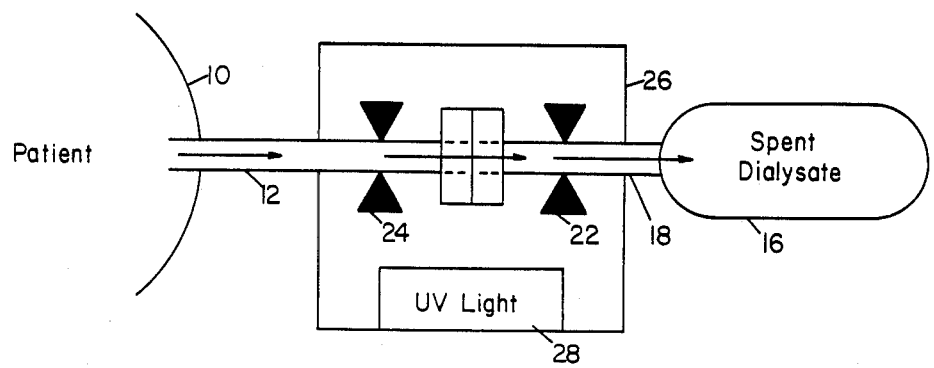
FIG. 7 illustrates the draining of spent dialysis fluid from the patient's peritoneal cavity.

If the emptied bag has been disconnected and the peritoneum access tube capped, a slightly different procedure is followed. First, the peritoneum access tube is uncapped and an empty bag is connected to the peritoneum access tube. Then, the potential contamination zone between clamps 22 and 24 is exposed to ultraviolet radiation to have an antimicrobial effect on the fluid flow path therethrough. As shown in FIG. 7, after irradiation of the potential contamination zone, clamps 22, 24 are released and spent dialysis fluid is drained from the patient's peritoneal cavity into bag 16. It is preferred that the potential contamination zone be irradiated prior to drain because of the potential retrograde movement of bacteria along tube 12 into the peritoneum, which potential increases if irradiation occurs for the first time simultaneous with the beginning of drain. In FIG. 7, the connected tubes 12 and 18 are shown as remaining in light box 26 while spent dialysis fluid is being drained. This is suitable. However, it is also suitable to remove the connected tubes from the light box during drain of the spent dialysis fluid.

Figure 8:
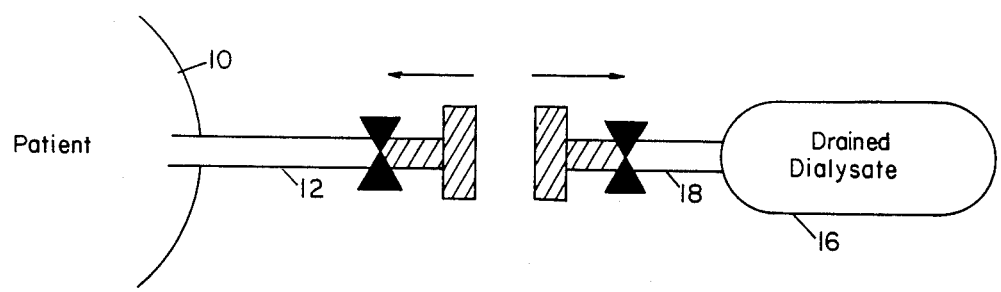
FIG. 8 illustrates the disconnection of the bag from the access tube following drainage.
Figure 9:
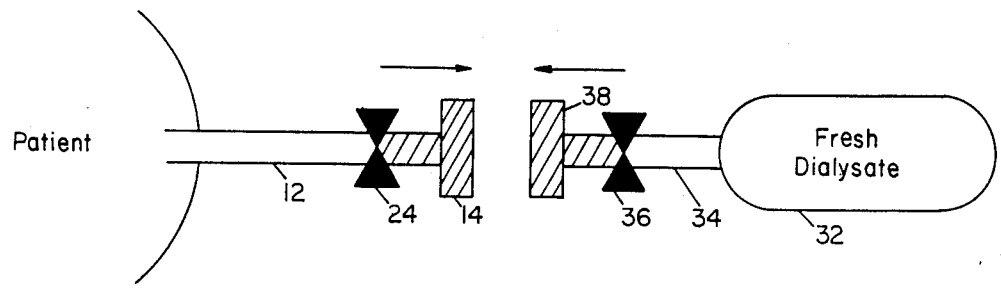
FIG. 9 illustrates the first step in repeating the procedure outlined by FIGS. 1-3.

After the fluid has been drained, tubes 12 and 18 are clamped and the now filled bag is disconnected from the peritoneum access tube, as indicated in FIG. 8. Then, as indicated in FIG. 9, a new bag 32 of fresh dialysis fluid is connected to the peritoneum access tube. FIG. 9 corresponds to FIG. 1 and represents the initial step in repeating the described method.

Figure 10:
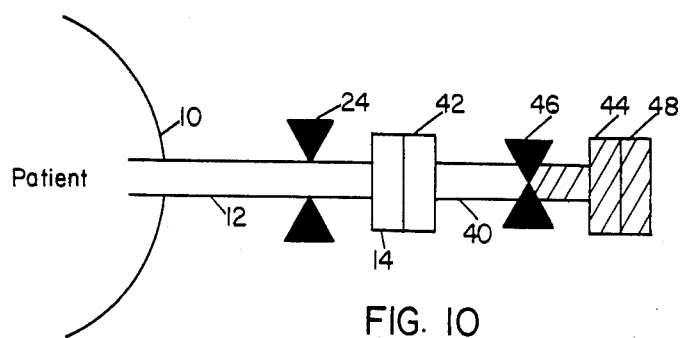
FIG. 10 is a schematic diagram of an alternate structure for the peritoneum access tube.

FIGS. 10-14 illustrate an alternative apparatus which can be used to practice the method of this invention. As shown in FIG. 10, a tubing segment 40 has connectors 42, 44 at opposite ends of tubing segment 40. A clamp 46 is provided on tubing segment 40. Connector 42 on tube segment 40 connects to connector 15 on catheter 11, while connector 44 on the opposite end of tubing segment 40 carries a cap 48. In carrying out the procedure shown in FIGS. 11-13, cap 48 of FIG. 10 would be removed and connector 52 on tube segment 50 would be connected to connector 44.

Figure 11:
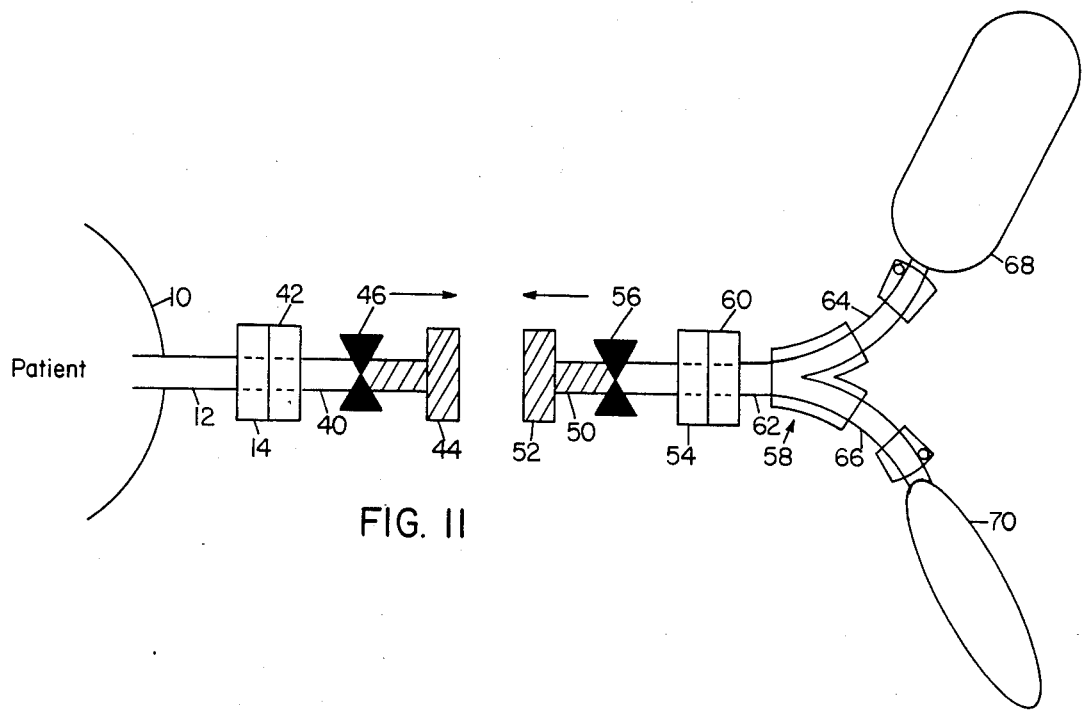
FIG. 11 is a schematic diagram of an alternate structure for carrying out CAPD using a branched tubing segment having both a bag of fresh dialysis fluid and an empty bag for receiving spent dialysis fluid.

Referring further to FIG. 11, there is illustrated an alternate apparatus for carrying out continuous ambulatory peritoneal dialysis on patient 10. In place of the single bag structure shown in FIG. 1, the alternate structure illustrated in FIG. 11 comprises a tube segment 50 having connectors 52, 54 at opposite ends and a clamp 56 intermediate the ends. A branched tubing segment 58, having connector 60 affixed to the end, connects with tubing segment 50 by means of engagement of connector 60 with connector 54. Branched tubing segment 58 includes base tubing segment 62 which branches into branch tubing segments 64 and 66. Branch tubing segment 64 connects to a first container 68, which may be a flexible, collapsable bag filled with fresh dialysis fluid. Branch tubing segment 66 connects to a second container, which may also be a flexible, collapsable bag, but which is empty and adapted to receive spent dialysis fluid drained from the patient. Bags 68 and 70 may be permanently affixed to branch tubing segments 64, 66; or alternatively, each bag 68, 70 may be removably connected to respective branch tubing segments 64, 66 by a connector.

Figure 12:
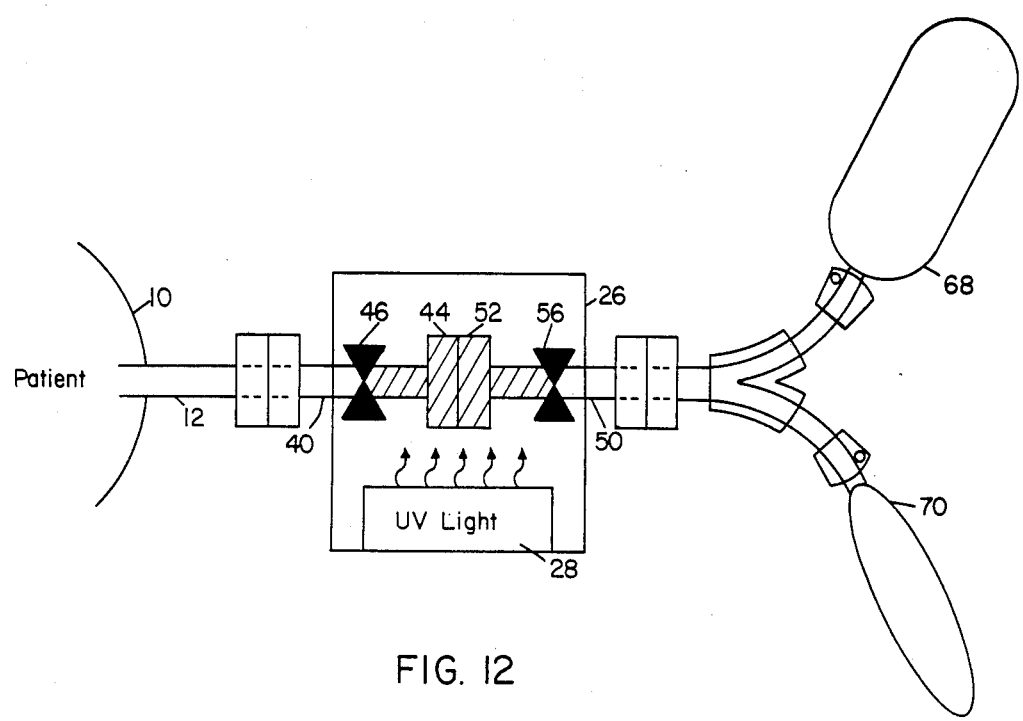
FIG. 12 illustrates irradiation with ultraviolet light of the connection between the access tube extension and the branched tubing segment.

To carry out continuous ambulatory peritoneal dialysis using the apparatus illustrated in FIG. 11, connector 52 is first connected to connector 44. Since connectors 44 and 52 are open, as are portions of tubing segments 40 and 50, up to the respective clamps 46, 56, there is potential contamination of that portion which is cross-hatched in FIG. 11. Accordingly, after connection of tubing segments 40 and 50, the potential contamination zone is placed in UV light box 26 and exposed to ultraviolet light; this step is illustrated in FIG. 12.

Figure 13:
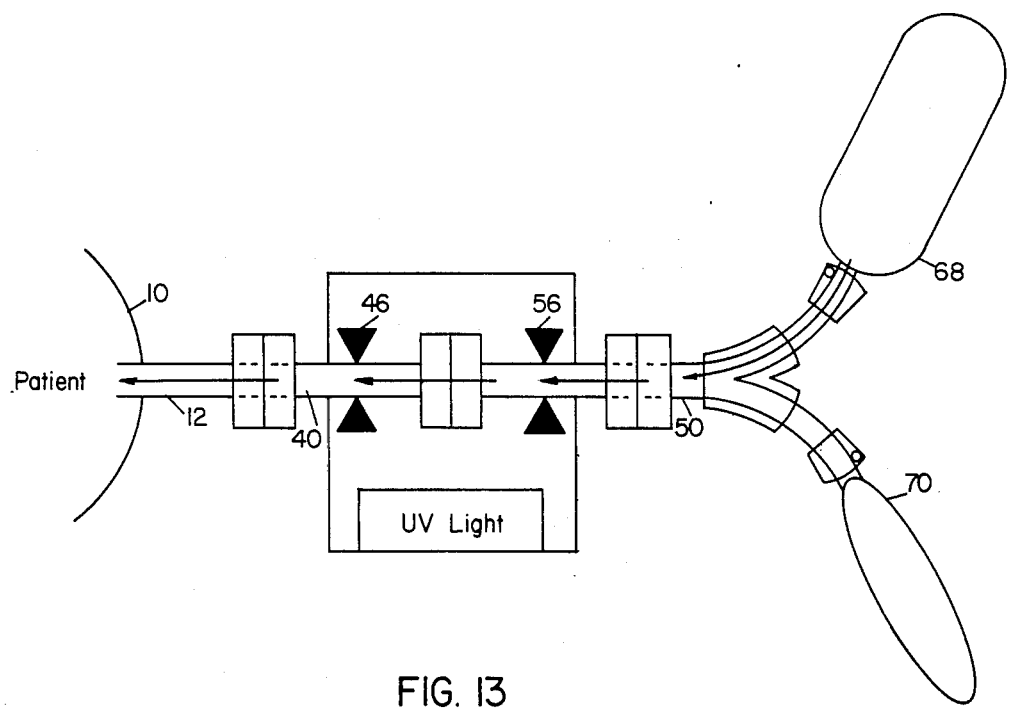
FIG. 13 illustrates the infusion of fresh dialysis fluid into the patient.

As represented by FIG. 13, after irradiation of the potential contamination zone, clamps 46 and 56 are opened, opening tube segments 40 and 50 to enable dialysis fluid flow from bag 68 after opening clamp 67. In this manner, infusion of fresh dialysis fluid into the patient takes place. If desired, irradiation of tubing segments 40 and 50 may continue during dialysis fluid infusion.

In the situation where the patient's peritoneal cavity is filled with dialysis fluid (which will be the typical situation regardless of whether the FIG. 1 or FIG. 11 apparatus is used), the cavity would, of course, first be drained, with the fluid going into bag 70 after clamp 69 is opened. Preferably, prior to drain, irradiation with UV occurs, and the irradiation may be continued during drain and the subsequent infusion from bag 68. It is recognized that regardless of whether a patient uses the apparatus of FIG. 1 or the apparatus of FIG. 11, some patients may desire to minimize the time required to complete the method of this invention. It may be possible to eliminate the necessity of irradiating prior to drain if adequate antimicrobial effect can be obtained and retrograde contamination prevented in the case where irradiation first begins simultaneous with the beginning of drain; thus no time would be added to the exchange procedure by irradiation.

Figure 14:
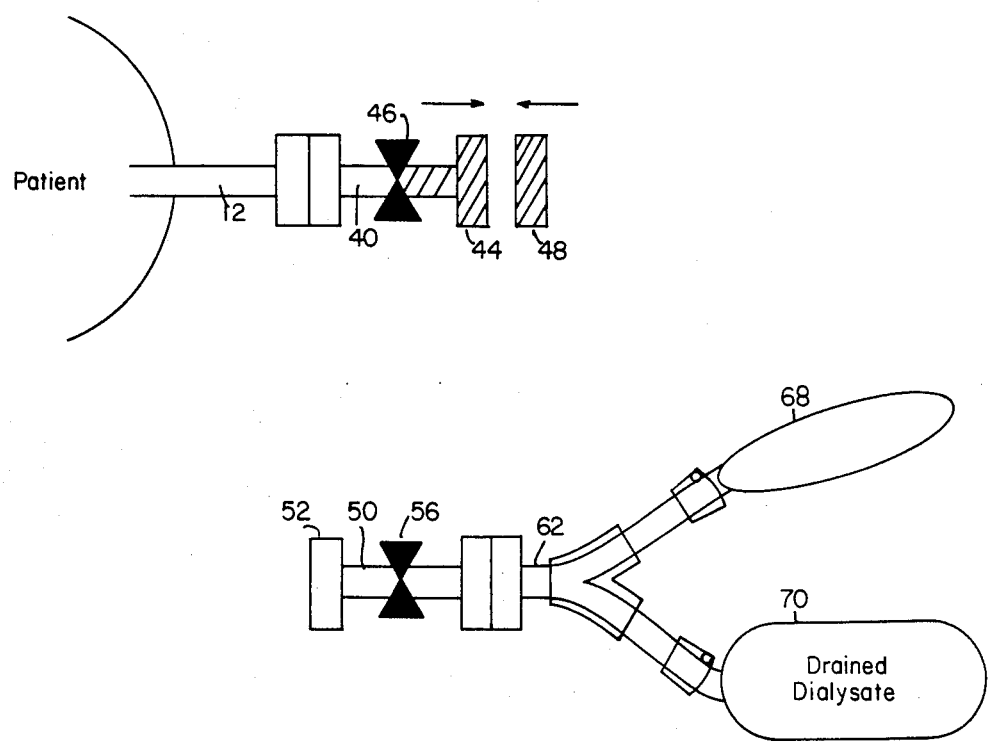
FIG. 14 illustrates the step of disconnecting the bags and tubing segments from the access tube.

In FIG. 14, there is illustrated the step of disconnecting tubing segments 50, 62, and bags 68, 70 from the access tube. This, of course, is accomplished by disconnecting connectors 44 and 52, after which connector 44 is covered with cap 48 ("capping off").

The tubing segments 50, 62 and bags 68, 70 may then be discarded.

The apparatus of FIG. 1 and FIG. 11 are distinguishable, and have comparative advantages and disadvantages. A patient selecting either the FIG. 1 or the FIG. 11 apparatus should be aware of the trade-offs. For example, although the FIG. 1 apparatus is simpler in design than FIG. 11, use of the FIG. 1 apparatus, with the patient also "capping off", will require two UV irradiations to complete the entire drain, infusion and dwell cycle; incidentially, this is the order in which drain, infusion, and dwell will most commonly occur when the entire patient population is considered.

Figure 6:
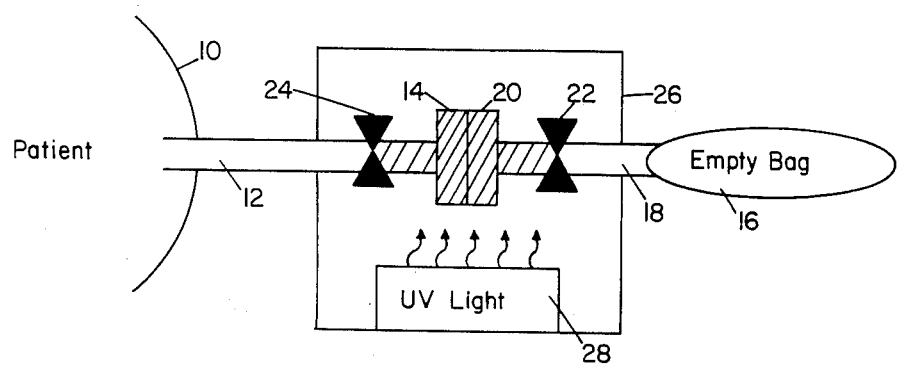
FIG. 6 illustrates irradiation of the connection between the bag and access tube after reconnection.

FIG. 2 shows one irradiation which is required using FIG. 1 apparatus: irradiation prior to infusion. FIG. 6 shows the second irradiation which is necessary if the patient "caps off": irradiation prior to drain.

Typically in an exchange procedure, irradiation prior to drain will occur before irradiation to infusion. There are a limited number of situations, however, in which a patient will infuse prior to drain, e.g., a new CAPD patient who has no dialysis solution in his peritoneal cavity. One of the prime advantages of CAPD is the nearly continuous presence of dialysis fluid in the peritoneal cavity providing a gentle continuous dialysis contributing to stable blood chemistries and the consequent general feeling of well-being experienced by CAPD patients.

The FIG. 11 apparatus has the potential advantage of requiring only one irradiation if the patient "caps off": irradiation prior to drain. This advantage is realized because of the branch tubing segmented design of FIG. 11 which leads to both drain and infusion bags. But most probably the FIG. 11 apparatus will be more expensive to manufacture than the FIG. 1 apparatus, and potentially a patient may find the FIG. 11 apparatus cumbersome to handle.

Figure 15:
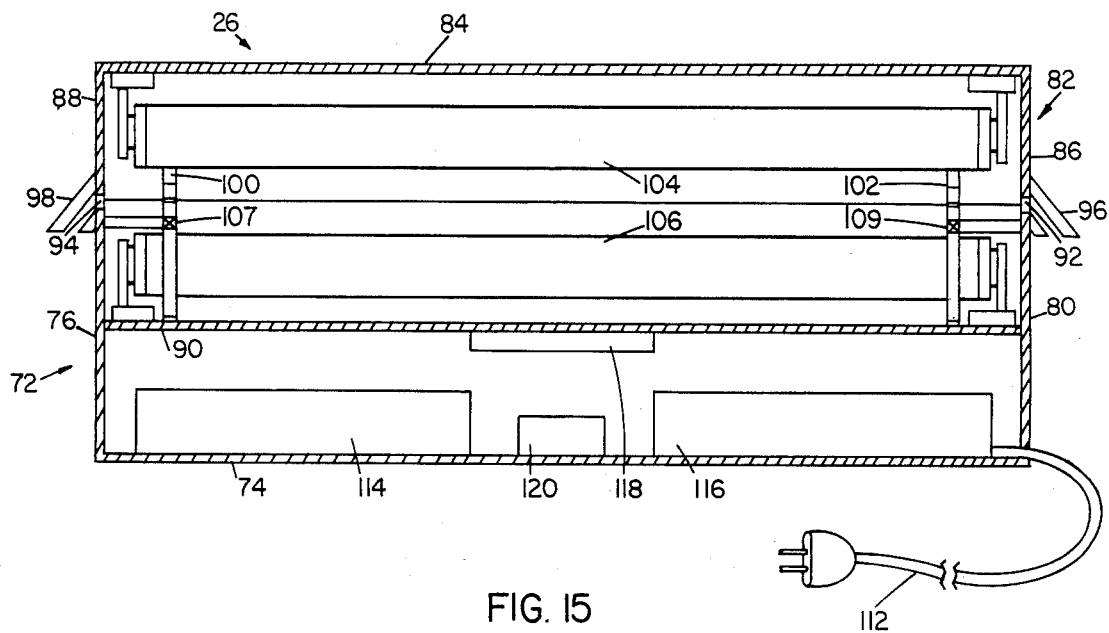
FIG. 15 is a cross-sectional side view of an embodiment of the UV light box shown in FIG. 2.

Referring to FIG. 15, there is shown in a cross-sectional side view apparatus for implementing the light box 26 shown in FIGS. 1-14. Light box 26 includes a base portion 72 having a bottom 74, front and back walls (not shown), and end walls 76, 80. Light box 26 also includes a hinged lid 82 adapted to be placed upon base portion 72. Lid 82 comprises a top 84, front and back walls (not shown), and end walls 86, 88. Light box 26 also has a shelf 90 disposed in base portion 72, shelf 90 extending horizontally between end walls 76, 80 and the front and back walls.

Openings 92 and 94 are provided in the end walls of the light box. Suitably, the openings are formed at the seam where the bottom edge of the lid end walls meet the top edge of the base portion end walls. Openings 92 and 94 are adapted to permit passage therethrough of tubing segments. For example, referring to FIG. 2, tubing segments 12 and 18 would pass through openings 94 and 92, respectively, with lid 82 closed. Disposed around opening 92 on the outside of box 26 is a light shield and tubing guide 96. Similarly, around opening 94 is a light shield and tubing guide 98. Internally of light box 26 and attached to the top side of shelf 90, are tubing clips 100 and 102. The clips stand vertically, and are provided to hold and properly position a connection junction and adjacent portions of access tube 12 and tube 18 along a prescribed axis. It is to be noted, however, that clips 100 and 102 do not correspond to clamps 22, 24 in FIG. 2.

Also contained internally of light box 26 are ultraviolet lamps. Suitably, four UV lamps are utilized. In FIG. 15, only lamps 104 and 106 are in view. Lamp 104 and another behind it, but not in view, are mounted in lid 84. Lamp 106 and another behind it, but not in view, are mounted in base portion 72.

Preferably, the interior surfaces of lid 82 and base portion 72 are covered with a layer of ultraviolet light reflective material. For example, polished aluminum could be used.

Figure 16:
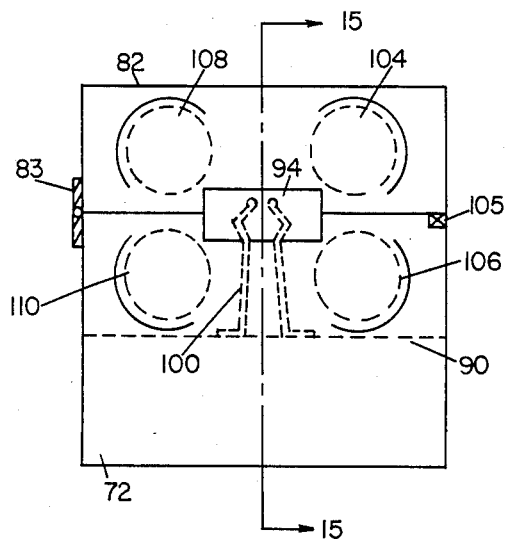
FIG. 16 is a cross-sectional end view of the light box shown in FIG. 15.

Referring to FIG. 16, there is presented a cross-sectional end view of light box 26. As shown therein, lid 82 is connected to base portion 72 by hinge connection 83. Also in view in FIG. 16 are UV lamps 108 and 110. The four UV lamps are symmetrically arranged around an axis defined by tubing clips 100, 102. Reflector shields 115, 117, 119 and 121 are also provided to direct lamp output radiation toward the axis defined by clips 100, 102.

Referring again to FIG. 15, beneath shelf 90 in base portion 72 is the electrical power and control circuitry for the UV lamps. Suitably, electrical power for the UV lamps is provided by an ac plug-in cord 112 and an internal power supply. Also included are lamp ballasts 114, 116, which are mounted to the bottom panel of base portion 72. Circuitry for controlling electrical power to the UV lamps is packaged and mounted to the under side of shelf 90.

Figure 17:
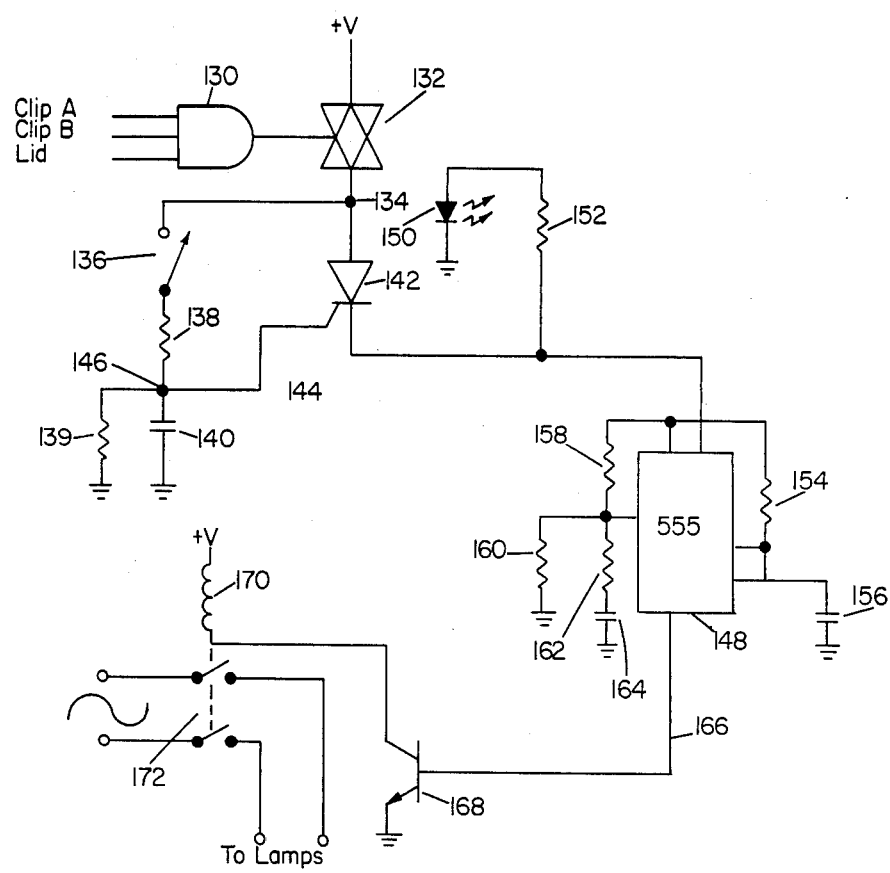
FIG. 17 is a schematic diagram of circuitry for controlling the operation of the UV lamps in the light box of FIGS. 15 and 16 based upon a prescribed elapsed exposure time.

Referring now to FIG. 17, there is presented one suitable implementation of electronic circuitry for controlling the UV lamps. The circuitry shown provides both on-off control and elapsed time control. Before discussing the specifics of the circuitry in FIG. 17, first to be described is the provision of microswitch 105 (see FIG. 16) to detect whether the lid is opened or closed, and microswitches 107, 109 (see FIG. 15) to detect whether tubing segments are properly positioned in the support clips. Microswitch 105 can be a contact microswitch which may be readily utilized in a conventional manner, as is well-known to those skilled in the field of electronics, to generate logic signals indicative of the open/closed status of the switch. For purposes of explanation in connection with FIG. 17, it is assumed that the microswitch 105 for detecting lid closure generates a high or logic "1" signal when the lid is closed. Also, it is assumed that the microswitches 107, 109 on the tubing segment support clips generate a high or logic "1" signal when the tubing segments are properly placed to receive UV radiation.

Continuing with reference to FIG. 17, the signals from the lid and support clip microswitches are applied to AND-gate 130. If a logic "1" is present on all three inputs to gate 130, a signal is produced which places electronic switch 132 in a conducting state and applies positive voltage to node 134. If, however, any one of the microswitch signals is a logic "0", switch 132 remains in the non-conducting state meaning there is a clip misalignment or lid closure problem. If desired, an indicator, for example a light emitting diode, can be connected to each of the gate 130 inputs to indicate the status of each microswitch signal, and thereby provide a visual means to enable the patient to determine if there is a clip misalignment or lid closure problem.

An irradiation cycle start switch 136 is connected to node 134. Connected in series with switch 136 is an RC network comprising resistor 138 and capacitor 140. The gate of SCR 142 is connected via conductor 144 to the connection node 146 of the components of the RC network. The anode of the SCR 142 is connected to node 134. The cathode of SCR 142 is applied to the voltage input of a timer circuit 148.

Closure of switch 136 applies electrical energy from the power source, for example, a dc power supply, to the RC network. Current flow through resistor 138 charges capacitor 140 to a voltage level sufficient to "gate-on" SCR 142. A conduction path is established through SCR 142 between the power supply and timer circuit 148. Energization of circuit 148 initiates its activity. Simultaneously, electrical power is applied to an indicator in the form of a light emitting diode 150 having a series-connected, currentlimiting resistor 152.

The RC network of resistors 138, 139 and capacitor 140 provides a short delay of a few milliseconds. The delay is optional and need not be included, in which case the gate of SCR 142 is connected directly to switch 136.

Timer circuit 148 may suitably comprise a NE555 integrated circuit device utilized in a monostable mode of operation. The timing period of the device's operation is established by an RC network comprising resistor 154 and capacitor 156. The RC network comprising resistors 158, 160, 162 and capacitor 164, which network is connected to the trigger input of device 148, provides the trigger input signal to initiate operation of the timer circuit. When triggered, timer circuit 148 changes its output state on line 166 and in effect "latches" into an "on" state.

The output signal available over line 166 from timer circuit 148 is applied to a transistor driver 168 which has coil 170 of a relay connected to the collector. Relay coil 170 controls relay contacts 172, which in turn controls the application of electrical power to the UV lamps.

The timer circuit is "on" for a period of time defined by the values of resistor 154 and capacitor 156, thus enabling control of the time the UV lights are on. This time period is, of course, selectable and serves as an elapsed time counter for an irradiation cycle.

Figure 18:
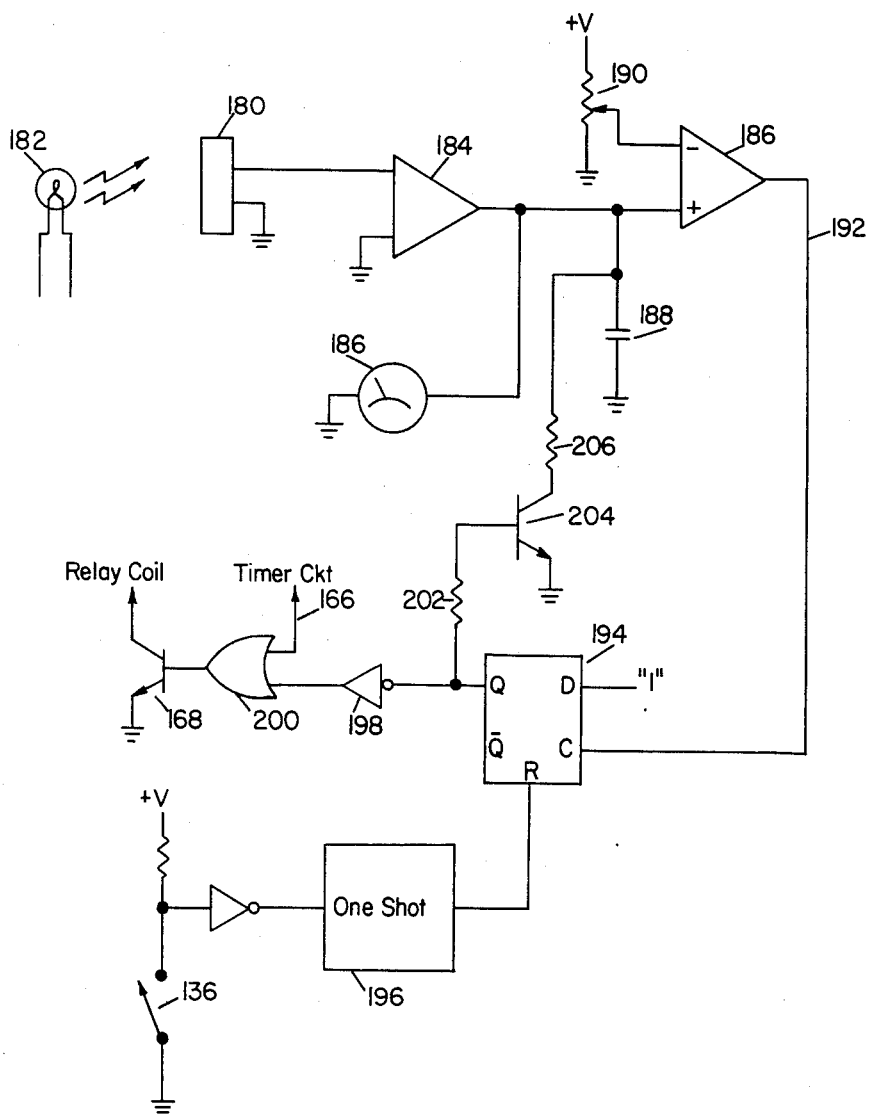
FIG. 18 is a schematic diagram of circuitry for controlling the operation of the UV lamps in the light box of FIGS. 15 and 16 based upon a predetermined amount of radiation exposure.

Referring now to FIG. 18, there is shown a schematic diagram of circuitry for controlling the electrical power to the UV lamps based upon measurement of the cumulative ultraviolet light exposure during each cycle. Exposure control may be utilized along with or as a substitute for elapsed time lamp control. Control of electrical power to the UV lamps based upon cumulative ultraviolet light exposure would compensate for lamp degradation over time.

Referring to FIG. 18, a UV light sensor 180 receives light from the UV lamps in the light box. For simplicity, the diagrammed lamp is labeled with reference numeral 182. The output signal generated by detector 180 is applied to an amplification block 184 which provides signal gain. The output of amplifier 184 is applied to a readout meter 186 which indicates the intensity level of the UV lamp 182. The output of amplifier 184 is also applied to the non-inverting input of a comparator 186. Also connected to the non-inverting input of comparator 186 is a shunt capacitor 188. The inverting input of comparator 186 is connected to the wiper of potentiometer 190, which sets the threshold level for the comparator.

The output signal from amplifier 184 charges capacitor 188. When a voltage is established on capacitor 188 which exceeds the reference level set by potentiometer 190, comparator 186 "switches" and produces a positive-going voltage transition on line 192. It will, of course, be appreciated that the rate at which capacitor 188 charges will be directly proportional to the intensity of light from lamp 182. Thus, as the lamp intensity decreases, the time required to charge capacitor 188 will increase.

The output of comparator 186 is used to clock flip-flop 194. At the beginning of an irradiation cycle, as initiated by closure of switch 136, one-shot 196 is triggered and produces a reset pulse to flip-flop 194. Resetting of flip-flop 194 establishes the Q output at a logic "0", which after inversion by inverter 198 applies a logic "1" to OR-gate 200. The output of OR-gate 200 provides turn-on drive to transistor 168 (also shown in FIG. 17). The second input to OR-gate 200 is line 166 from timer circuit 148 in FIG. 17.

When there has been sufficient ultraviolet light exposure of a potential contamination zone, for example, as shown in FIG. 2, capacitor 188 will have charged to the voltage necessary to effect switching of comparator 186. The output voltage transition from comparator 186 clocks flip-flop 194 setting the Q output to a logic "1". Inversion of this signal by inverter 198 produces a logic "0" which is ineffective to cause OR-gate 200 to turn on transistor 168. The logic "1" condition of the Q output of flip-flop 194 is also applied via resistor 202 to transistor 204. The collector of transistor 204 is connected through resistor 206 to capacitor 188. The logic "1" condition on the Q output causes transistor 204 to turn on and discharge capacitor 188 to condition it for the next irradiation cycle.

It will be appreciated that although timer circuit 148 in FIG. 17 may "time-out" indicating that the desired elapsed time has expired, if the cumulative ultraviolet light exposure has not reached a certain minimum level, as established by the reference voltage on the inverting input of comparator 186, OR-gate 200 will continue to apply turn-on drive to transistor 168 until the cumulative exposure level has been attained and flip-flop 194 is clocked.

The foregoing description has been of particular implementations of the present invention for purposes of explanation and illustration. It will be apparent to those skilled in this art that many modifications and changes in the implementations shown may be made without departing from the basic teachings of the present invention. Accordingly, that subject matter, and all equivalents thereof, which Applicants regard to be their invention is set forth in the following claims.

What is claimed is:

1. A method of peritoneal dialysis therapy of a patient having a peritoneum access tube extending through the abdominal wall, for establishing a fluid flow path to the peritoneal cavity, comprising the steps of:
   connecting a container of fresh dialysis fluid to said peritoneum access tube;
   irradiating the connection junction between the container and the access tube with a sufficient quantity of ultraviolet radiation so that an antimicrobial effect is obtained at said connection junction; and
   infusing the fresh dialysis fluid into the patient.

2. The method of claim 1 wherein said irradiating step is continued during the infusion of the dialysis fluid.

3. The method of claim 1 further comprising the steps of:
   allowing the dialysis fluid to remain within the patient's peritoneal cavity for a residence time period;
   draining the dialysis fluid from the patient's peritoneal cavity after the residence time period; and
   disconnecting said container from said access tube.

4. A method of peritoneal dialysis therapy of a patient having an indwelling catheter implanted in his peritoneal cavity and extending through his abdomen, said catheter interconnected with an access tube, comprising the steps of:
   connecting an empty container to the access tube;
   irradiating a potential contamination zone between the indwelling catheter and said empty container, including at least a portion of the access tube, with a sufficient quantity of ultraviolet radiation so that an antimicrobial effect is obtained in said potential contamination zone;
   draining dialysis fluid from the patient's peritoneal cavity and into the empty container through the access tube;
   disconnecting the now-filled said empty container;
   connecting a source of fresh dialysis fluid to the peritoneum access tube; and
   infusing said dialysis fluid into the patient's peritoneal cavity through the access tube.

5. A method of peritoneal dialysis therapy of a patient, comprising the steps of:
   establishing a fluid flow path to the peritoneal cavity of the patient;
   connecting a container of fresh dialysis fluid to said fluid flow path;
   irradiating the connection junction between the container and the fluid flow path with a sufficient quantity of ultraviolet radiation so that an antimicrobial effect is obtained on said connection junction;
   infusing said dialysis fluid into the patient's peritoneal cavity through the fluid flow path;
   allowing the dialysis fluid to remain within the patient's peritoneal cavity for a residence time period; and
   draining the dialysis fluid from the patient's peritoneal cavity after the residence time period.

6. A method of performing peritoneal dialysis on a patient by adding fresh peritoneal dialysis solution to the peritoneal cavity of a patient in a manner that decreases the likelihood of transmitting microbial contamination to the peritoneal cavity of the patient, the method comprising the steps of:
   connecting a first container filled with fresh peritoneal dialysis solution, and a second container which is empty, to a conduit in flow communication with the patient's peritoneal cavity; exposing at least the connection junction between the conduit and the containers to a sufficient quantity of ultraviolet radiation so that an antimicrobial effect is obtained at said connection junction; flowing fresh peritoneal dialysis solution from the first container into the patient's peritoneal cavity via said conduit; and therafter draining spent peritoneal dialysis solution from the patient's peritoneal cavity via said conduit into said empty container.

7. Apparatus for interconnection with a catheter and access tube communicating with the peritoneal cavity of a patient for conducting continuous ambulatory peritoneal dialysis, which comprises:
   a tubing segment including a branched tubing portion having a first and second branches which respectively communicate with a first container filled with peritoneal dialysis solution and a second empty container;
   an aseptic connector at one end of said tubing segment for connection to the catheter access tube;
   a clamp for controlling flow through said tubing segment and isolating said branched tubing portion from the connector to create an aseptic barrier when the connector is disconnected; and
   an ultraviolet light applicator means for irradiating at least the portion of the tubing segment between the connector and the clamp.

* * * * *